(12) United States Patent
Keefe et al.

(10) Patent No.: US 8,636,202 B2
(45) Date of Patent: Jan. 28, 2014

(54) FIRST TIME CONFIRMATION OF DATABASE ENTRY

(75) Inventors: Gary Keefe, Brecksville, OH (US); Alan Gilbert, Hudson, OH (US)

(73) Assignee: Codonics, Inc., Middleburg Heights, OH (US)

( * ) Notice: Subject to any disclaimer, the term of this patent is extended or adjusted under 35 U.S.C. 154(b) by 0 days.

(21) Appl. No.: 13/357,669

(22) Filed: Jan. 25, 2012

(65) Prior Publication Data

US 2013/0186950 A1    Jul. 25, 2013

(51) Int. Cl.
*G06F 17/00* (2006.01)

(52) U.S. Cl.
USPC .......................................... 235/375; 235/380

(58) Field of Classification Search
CPC ....... G06Q 50/24; G06Q 30/16; G06Q 50/22; G06F 19/322; G06F 19/326; G06F 19/327; G06F 19/3443

USPC .......................... 235/375, 494, 492, 380, 486
See application file for complete search history.

(56) References Cited

U.S. PATENT DOCUMENTS

| | | | |
|---|---|---|---|
| 7,657,443 B2* | 2/2010 | Crass et al. ...................... 705/2 |
| 2011/0066260 A1* | 3/2011 | Condurso et al. ............... 700/83 |
| 2011/0093279 A1* | 4/2011 | Levine et al. ..................... 705/2 |
| 2011/0180441 A1* | 7/2011 | Bach .......................... 206/459.5 |

* cited by examiner

*Primary Examiner* — Thien M Le
(74) *Attorney, Agent, or Firm* — Pearne & Gordon LLP

(57) ABSTRACT

Provided is an apparatus that stores a formulary. The apparatus includes a memory device that stores the formulary, the formulary comprising a plurality of drug entries. A user input device allows a user to verify a drug of the plurality of drug entries of the formulary. A code reader interprets computer-readable codes. After a computer-readable code that is associated with the drug is read by the code reader, the drug is verified using the user input device.

17 Claims, 5 Drawing Sheets

FIRST TIME CONFIRMATION OF DATABASE ENTRY

BACKGROUND OF THE INVENTION

1. Field of the Invention

This application relates to drug databases used in medical facilities, and to devices and methods employing such databases.

2. Description of Related Art

Medical facilities, such as hospitals, can have a pharmacy that stores drugs used within the facility. The drugs are dispensed under the supervision of a pharmacist. For example, the pharmacist might dispense drugs from the pharmacy to an anesthesiologist for use during a surgical procedure.

Information about various drugs including, but not limited to, the drugs stored in the pharmacy, can be saved in a database (e.g., a master drug database "MDD"). The MDD is accessible to authorized users in the medical facility, such as the pharmacist. To facilitate inventorying and tracking of drugs within the medical facility, the drugs can be identified by computer-readable codes, as provided by barcodes, radio-frequency identification (RFID) tags, or other types of codes capable of being read in a non-contact manner. The database can store information about a particular drug, such as a drug name, concentration, expiration date, etc., in association with a particular computer-readable code for the drug. Such information can be retrieved from the database when the code is read by a device capable of interpreting such codes (i.e., "a code reader"). Example code readers include barcode scanners, RFID readers and the like.

Since a computer-readable code is not easily interpreted by a person, labeling errors can go undetected. For example, a barcode associated with a first type of drug could unknowingly be placed on a second type of drug. When the barcode is subsequently scanned, information about the first type of drug will be retrieved from the database. This could lead a person to who is actually administering or dispensing the second type of drug to erroneously believe that they are administering or dispensing the first type of drug. Similarly, errors in the database itself could lead to a barcode for the first type of drug being placed onto a second type of drug.

BRIEF SUMMARY OF THE INVENTION

Accordingly, it would be desirable to verify the drug in the database and/or verify information about the drug.

According to one aspect, provided is an apparatus that stores a formulary. The apparatus includes a memory device that stores the formulary, the formulary comprising a plurality of drug entries. A user input device allows a user to verify a drug of the plurality of drug entries of the formulary. A code reader interprets computer-readable codes. After a computer-readable code that is associated with the drug is read by the code reader, the drug is verified using the user input device.

According to another aspect, provided is a method of confirming drug information. A plurality of drug entries, each associated with a computer-readable code, are received. The plurality of drug entries are stored on a memory device. A code reader reads the computer-readable code associated with a drug of the plurality of drug entries. A user is automatically prompted to verify the drug after reading, by the code reader, the computer-readable code associated with the drug. An input is received from the user verifying the drug.

BRIEF DESCRIPTION OF THE DRAWINGS

The invention may take physical form in certain parts and arrangement of parts, embodiments of which will be described in detail in this specification and illustrated in the accompanying drawings which form a part hereof and wherein.

DETAILED DESCRIPTION OF THE INVENTION

Figure 1:
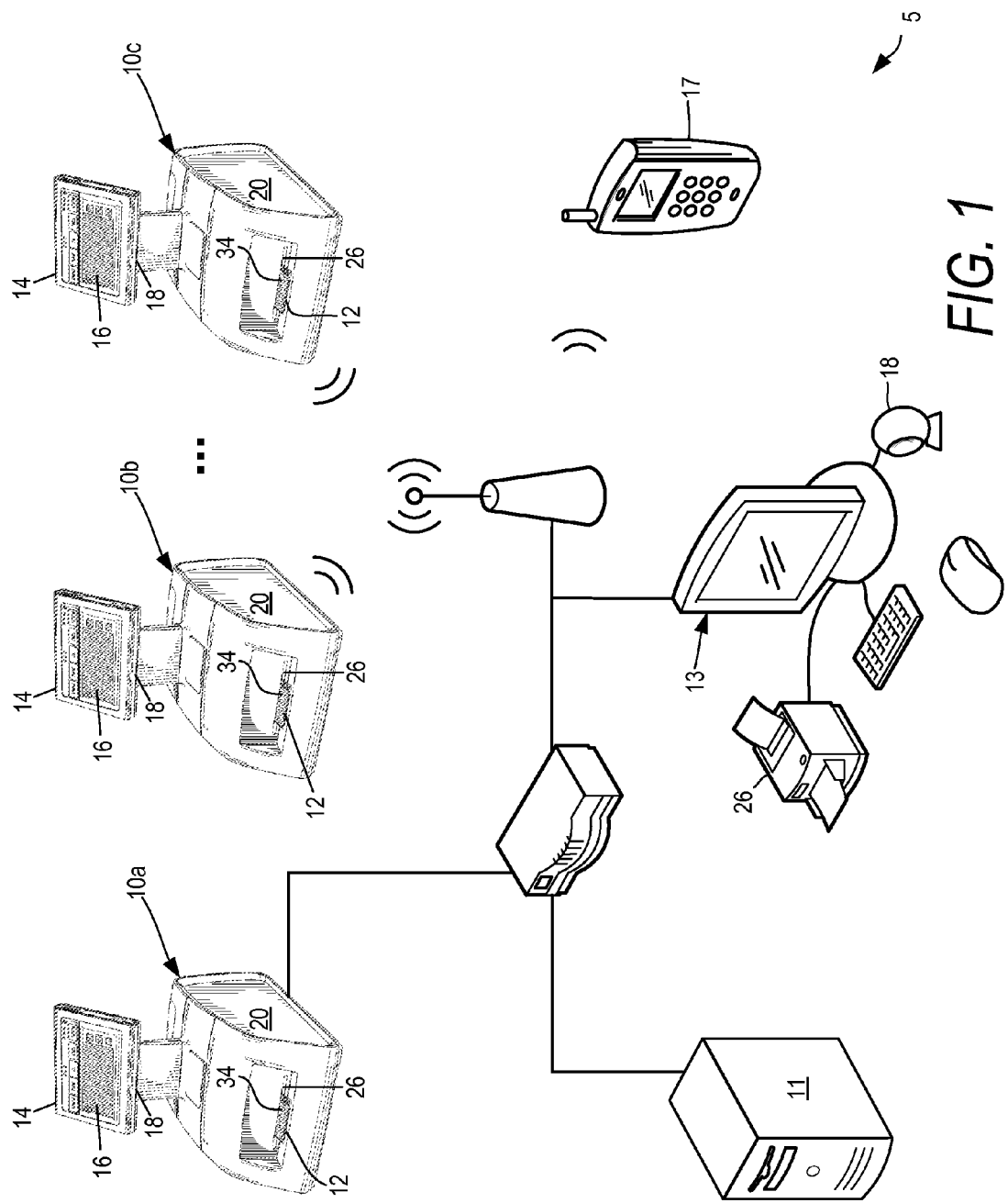
FIG. 1 is a schematic diagram of a portion of a medical computer network for generating a label to be applied to a container storing a medicinal substance.

Certain terminology is used herein for convenience only and is not to be taken as a limitation on the present invention. Relative language used herein is best understood with reference to the drawings, in which like numerals are used to identify like or similar items. Further, in the drawings, certain features may be shown in somewhat schematic form.

It is also to be noted that the phrase "at least one of", if used herein, followed by a plurality of members herein means one of the members, or a combination of more than one of the members. For example, the phrase "at least one of a first widget and a second widget" means in the present application: the first widget, the second widget, or the first widget and the second widget. Likewise, "at least one of a first widget, a second widget and a third widget" means in the present application: the first widget, the second widget, the third widget, the first widget and the second widget, the first widget and the third widget, the second widget and the third widget, or the first widget and the second widget and the third widget.

FIG. 1 shows a portion of a medical labeling network 5. The network includes a plurality of operating room ("OR") computer terminals 10a, 10b, 10c (referred to generally at 10), a database server 11, and a pharmacy computer terminal 13. The computer terminal 10 is referred to as an OR computer terminal out of convenience, to explain the drawings in the context of a medical facility (e.g., a hospital). The OR computer terminal 10 can, but need not be, located in an operating room or otherwise associated with an operating room where a surgical procedure can be performed on a patient.

A master drug database ("MDD") is stored on the database server 11. Alternatively, the MDD can be stored on the pharmacy computer terminal 13. The MDD can contain an identity, identification code (e.g., NDC) number, concentration, any other pertinent information for drugs used in the hospital, or any combination thereof. The pharmacy computer terminal 13 can execute computer-executable instructions embodied as a software program stored in a computer memory provided to the pharmacy computer terminal 13 called an administration tool ("AT"). The AT can be used by a pharmacist to create and distributed a formulary including a subset of the entries found in the MDD to the OR computer terminals 10. The AT can also optionally be used to retrieve drug information from the MDD, update the MDD (e.g., add new drugs to the database or modify existing drug information), etc.

Figure 3:
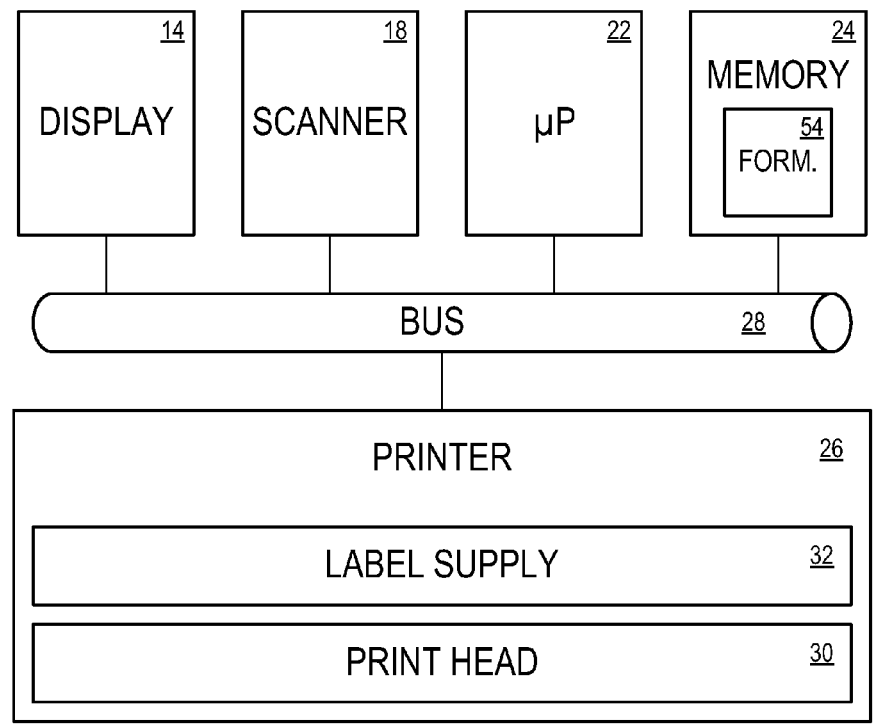
FIG. 3 shows a block diagram of the example computer terminal.

Based on information contained in the MDD, the pharmacist creates and manages a formulary 54 to be stored in a memory device 24 (see FIG. 3) of one or more of the OR computer terminals 10, as described in detail in U.S. patent application Ser. No. 13/274,184, which is hereby incorporated in its entirety by reference herein. The formulary can include a subset of the MDD selected and added to the formulary 54 using the AT, and the subset can optionally comprise those drugs that are commonly used in the operating room or other location at the medical facility where the OR computer terminal 10 is positioned. The same formulary can optionally be stored in the memory device 24 of more than one computer terminal, and can optionally be customized to include drugs utilized during surgical procedures relating to a particular medical discipline. For example, the same formulary comprising drugs commonly used during cardiac surgical procedures may be stored in the memory device 24 of multiple computer terminals, which are each located in a respective operating room dedicated for such procedures. Another, different formulary comprising drugs, optionally in appropriate doses, suitable to be administered to children can be stored in the memory of a computer terminal located in an operating room dedicated for pediatric surgical procedures. According to alternate embodiments, the formulary 54 stored in the memory device 24 of the OR computer terminal 10 can be evaluated and updated, replaced or otherwise changed before each surgical procedure if the operating room where the OR computer terminal 10 is located is not dedicated for a particular type of surgical procedure.

When a formulary update is needed to accommodate a specific type of procedure, a pharmacist or other authorized individual can create a new or updated formulary with the AT. The new or updated formulary, once complete, can be transmitted over the network 5 (e.g., LAN, WAN or both) in FIG. 1 to each of the OR computer terminals 10 that are to replace the existing formulary in the memory device 24 in of the OR computer terminal 10 with the new or updated formulary. The new or updated formulary can be transmitted from the pharmacy computer terminal 13 to the OR computer terminal 10 via the network 5 or, according to alternate embodiments, can be transferred to the OR computer terminal 10 from a portable memory device, such as a USB flash memory for example. Once transmitted to the OR computer terminal 10, the formulary is available to be used by the OR computer terminal 10 to relate computer-readable codes scanned as described below to a drug in the formulary. Thus, the OR computer terminal 10 can identify drugs based on such computer-readable codes without operator intervention.

One or both of the OR computer terminal 10 and the administration tool AT on the pharmacy computer terminal 13 provide the user (e.g., pharmacist, doctor, etc.) with an opportunity to verify a drug in the formulary. The verification can occur before the drug is entered into the formulary or after the drug is entered into the formulary using the AT on the pharmacy computer terminal 13, and can occur before the formulary is created, while the formulary is being created, or after the formulary is created. Drug verification can also optionally be performed using the AT before the formulary is transmitted to the OR computer terminal 10, using the OR computer terminal that has already received the formulary, or a combination thereof. Regardless of where verification is received from a user, e.g., with the OR computer terminal 10, with the AT running on the pharmacy computer terminal 13, or elsewhere in a network, once a drug included in a formulary has been verified as being correctly identified by a computer readable code, the fact that verification has occurred for that drug can be indicated in the formulary so the next time that drug is subsequently identified by a computer readable code verification can be omitted (i.e., not required subsequent to first time verification).

Verifying the drug involves receiving, with the OR computer terminal 10, the pharmacy computer terminal 13, or other computer terminal, manually-input confirmation from a user that drug information returned in response to scanning a computer-readable code does indeed correspond to the drug associated with that computer-readable code. For example, a label applied to a drug vial storing propofol may include a barcode that is to be scanned by a code reader 18 such as a barcode scanner provided to the OR computer terminal 10 or pharmacy computer 13. In response to scanning that barcode, the OR computer terminal 10 or pharmacy computer 13 interprets the barcode to determine an identification number and retrieves an entry from the formulary assigned to that identification number. The relevant information of that entry can be displayed by a display connected to the OR or pharmacy computer terminal, audibly broadcast via a speaker, or a combination thereof. The user can compare the returned drug information with drug information printed on the label on the drug vial to make sure that they match. The drug information stored in the MDD or formulary can be displayed on a display device at the pharmacy computer terminal 13 or the OR computer terminal 10, or audibly broadcast by a speaker at such computer terminals, or printed by a printer 26 at such computer terminals. The display device and speaker are example interface devices for conveying drug information to a user. The user can confirm that drug information printed on the drug's container or packaging matches the information in the MDD or formulary through an input device (e.g., push button, soft key, etc.) at the pharmacy computer terminal 13 or the OR computer terminal 10. The interface device and the input device can optionally be integrated in a common user interface.

Figure 4:
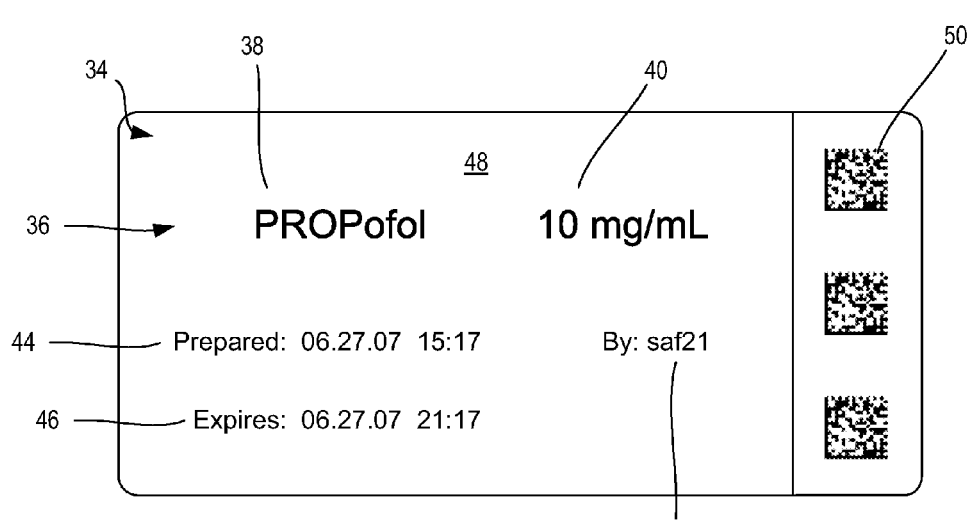
FIG. 4 shows an example medical label.

In certain embodiments, the pharmacy computer terminal 13 and the OR computer terminal 10 include code readers (e.g., barcode readers, RFID readers, etc.) that read computer-readable codes associated with the drugs in the MDD and formulary. As an example, FIG. 4 illustrates a label that can be applied to a drug vial or other drug packaging including a barcode 50, which in the present example is a Data Matrix two-dimensional barcode. When the barcode 50 is scanned by the code reader, the pharmacy computer terminal 13 or OR computer terminal 10 that communicates with the code reader can retrieve and display drug information associated with the barcode. The user can then manually input verification that the retrieved drug information matches the information printed on the drug's container or packaging.

The interface device at the pharmacy computer terminal 13 and/or the OR computer terminal can prompt the user to verify that a drug entry in the formulary matches the drug information printed on the drug's container or packaging. For example, a display device such as a computer monitor, for example, can display an instruction to verify the retrieved drug information, or the speaker can broadcast such an instruction. The prompt can optionally be limited to occurring a single time, such as the first time the drug information is retrieved from the formulary in response to scanning a barcode, or optionally multiple times, such as each time drug information is retrieved from the formulary in response to scanning a barcode. In certain embodiments, an interface device is controlled to automatically generate the prompt seeking manual verification from the user after the drug's computer readable code is first read by the code reader. The OR computer terminal 10 and/or pharmacy computer 13 can optionally not prompt the user for verification once the drug information in that formulary has been verified at least once by an authorized user. That is, the drug's computer readable code can be subsequently read again by the code reader after verification has been received and associated with the verified drug entry in the formulary without the prompt being generated again.

Once the user verifies the drug, successful verification can be stored in the formulary for that particular drug entry in the memory 24 of the OR computer terminal 10 where verification was performed. According to alternate embodiments, successful verification can optionally be transmitted via the network 5 to be stored in association with that drug entry in the formulary stored by the memory of each OR computer terminal 10 in a network such as a private LAN of a given medical facility, for example. Thus, each formulary stored by an OR computer terminal 10 having that particular drug entry can receive and store confirmation of successful verification to avoid requiring a user of those recipient OR computer terminals 10 from being prompted for verification the first time the drug entry is returned in response to scanning a machine-readable code associated with that drug. According to another embodiment, notice that verification of a drug entry has occurred at the OR computer terminal 10 can optionally be transmitted via email, text message, or other network communication to the pharmacy computer terminal 13; a handheld portable communication device 17 (FIG. 1) (e.g., mobile phone, personal digital assistant ("PDA"), etc. . . . ) designated for use by a person authorized to access and edit the formulary such as a pharmacist, for example. By transmitting notification that verification has been received by one or more of the OR computer terminals 10, the pharmacist can ensure verification of that particular drug entry is included in the formulary 54 before the formulary 54 is distributed to the OR computer terminal(s) 10 in the future as part of a new formulary that is to entirely replace an existing formulary.

As mentioned above, manual verification of drug entries in a formulary 54 can optionally occur before the formulary 54 is delivered to the OR computer terminals 10. According to those embodiments, the pharmacist can use a barcode scanner or other input device to read barcodes or other machine-readable codes associated with each drug entry in the formulary 54 to be verified. Those drug entries that are verified can include a record to that effect in the formulary, and the first time verification of those drug entries can be omitted once the formulary 54 is delivered to the OR computer terminals 10. In this manner, the users of the OR computer terminals 10 may optionally not be prompted for manual verification the first time a barcode or other machine-readable code is scanned for the verified drug entries.

Embodiments of the OR computer terminal 10 can optionally allow for bypassing first time verification. According to such embodiments, the OR computer terminal 10 can prompt the user to input verification via the touch screen display 14 or other input device provided to the OR computer terminal 10. The options presented, however, can also include a bypass command that, if selected, allows printing of a label as described below to proceed without verification. A user who elects to bypass verification and trust the drug information returned in response to scanning a barcode on a drug vial can continue with the process of printing a label. However, a record is created by the OR computer terminal 10 indicating that verification was bypassed. The user of the OR computer terminal can also optionally be required to be logged into the OR computer terminal 10, so the identification of the authorized user who elects to bypass verification can also be included in the record documenting the selection of the bypass option. Other information such as the drug entry in the formulary, concentration, date, patient who received the drug for which verification was bypassed, etc. . . . can also optionally be included in the bypass record.

Figure 2:
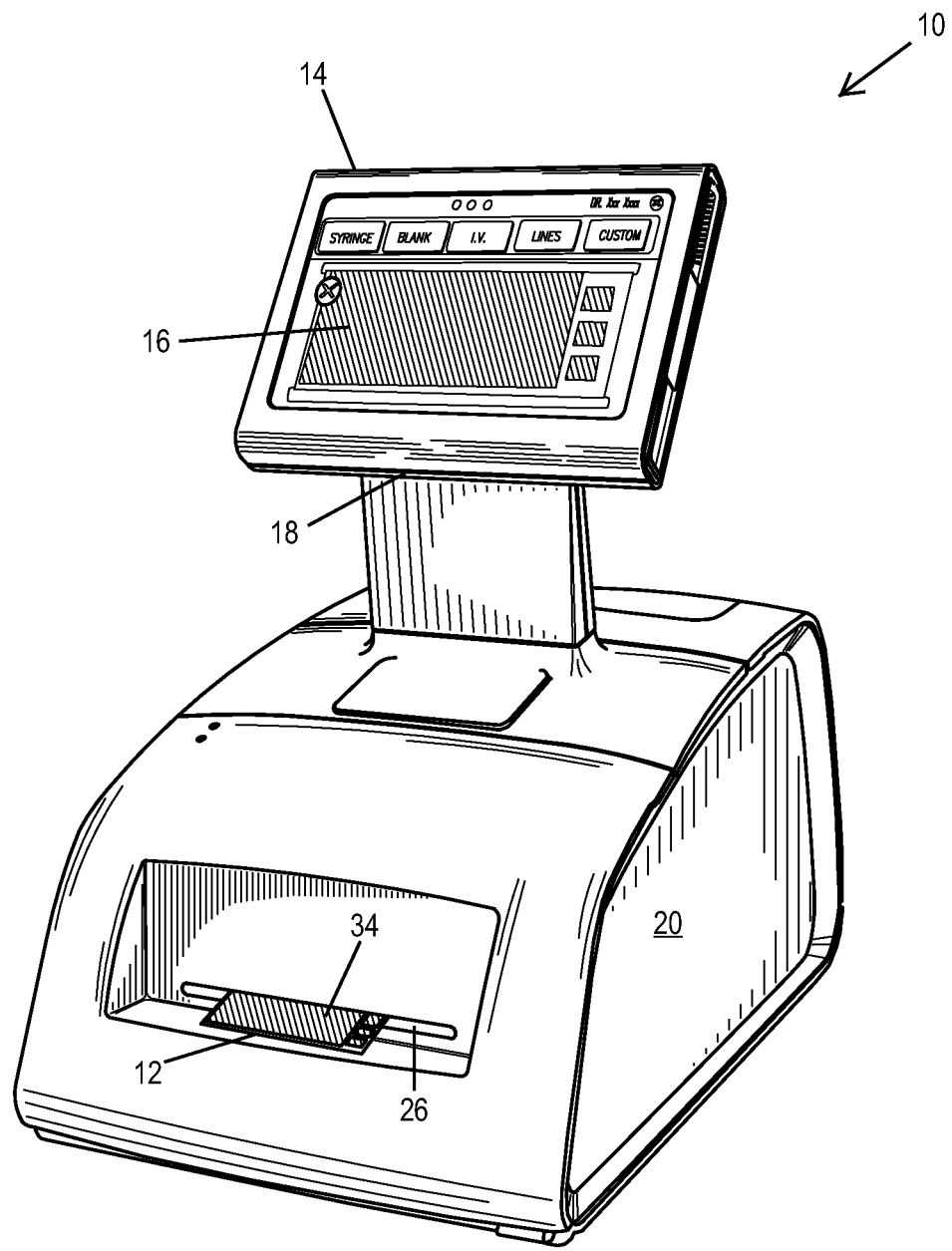
FIG. 2 is a perspective view of an example computer terminal of the medical computer network.

In addition to receiving user verification of a drug, the OR computer terminal 10 is capable of generating a label identifying the drug, from information in the formulary. In particular, the label printed can be required to conform to a labeling standard observed in the medical field governing the labeling of that drug. As shown in FIG. 2, the OR computer terminal 10 includes a touch-screen display 14 that displays a virtual label 16 to be printed as the label 12, and displays soft keys that can be touched by a user to input data and commands into the OR computer terminal 10, such as the verification command discussed above. The virtual label 16 is a computer-generated rendering of the label 12 that offers the user visual confirmation of the appearance of the physical label 12 to be printed by a printer 26, and when verification is required, the virtual label 16 can optionally be compared to the label bearing the barcode scanned to generate the virtual label 16 for verification purposes. A code reader 18 can be provided at a convenient location such as adjacent a bottom portion of the display 14 to read a computer-readable code.

The OR computer terminal 10 includes a cabinet 20 housing components that are operable to produce the label 12 in compliance with a medical labeling standard. The cabinet 20 can also support the display 14 and the code reader 18 to form a self-contained, stand-alone and monolithic unit. However, alternate embodiments include at least one of the display 14, the code reader 18 and a printer 26 provided separately from the cabinet 20, to be positionable relative to the cabinet 20 as a peripheral that is operatively connected to the other components supported by the cabinet 20. The internal components housed within the cabinet 20 are schematically illustrated by the block diagram of FIG. 3. A computer processor 22 is provided to execute computer-executable instructions stored in a non-transitory computer readable memory 24 such as a hard disk drive, read-only memory ("ROM"), random access memory ("RAM"), optical disc, or any other suitable memory device. The formulary 54 is also stored in the memory 24. A bus system 28 facilitates communication between components such as the display 14, code reader 18, processor 22, memory 24 and printer 26.

The printer 26 includes a print head 30 for applying label content onto label stock delivered from a supply 32 of labels, which can be blank, or at least in partial compliance with a medical labeling standard. The print head 30 can fall within any category of printing technology suitable to apply label content onto label stock. For example, the print head 30 can be an inkjet print head that deposits droplets of ink in a pattern to create the label content, a laser print head that directs a laser across a photoreceptor to create the pattern for the label content to be printed, a solid-ink print head, a dot matrix print head, and the like.

The label supply 32 can include a roll of label stock that has blank labels supported on a release tape, a tray of individual blank labels, or any other source of labels on which label content is to be printed. The label supply 32 can be internally disposed within the printer 26 or fed into the printer from an external location.

FIG. 4 shows an illustrative embodiment of a label 12 to be generated by the OR computer terminal 10. The label 12, as shown, includes label content that is compliant with, and renders the label 12 compliant with a medical substance labeling standard. For example, the medicinal substance labeling standard can be the guidelines promulgated by the National Safety Patient Goals of the Joint Commission, the American Society of Anesthesiologists, any other medicinal labeling standard established by a professional governing or trade organization or a governmental organization, or any combination thereof. Such guidelines can be based on other medicinal substance labeling standards such as those created by ASTM International, for example. The medicinal substance labeling standards can also require specific sizes, colors and patterns, type faces and other label content used on labels applied to unlabeled syringes that are filled by the users (i.e., those who will administer the medicinal substance to the patient) or their agents to identify the medicinal substance. Such standards are typically not intended to govern the requirements of labels applied by the drug manufacturer.

The label content required to render the label 12 compliant with a labeling standard created to govern the labeling of any material in the medical field can be specific to the particular standard against which compliance is to be measured. For instance, depending on the medicinal substance labeling standard, the label content can include one, a plurality, or all of the following:

a concentration of a drug to be identified by the label 12,
a dilution of a drug and a diluent used to dilute the drug;
a date and/or time at which the drug was prepared;
an expiration date and/or time of the drug to be labeled;
an identification of an individual who prepared the drug;
a warning about a risk associated with the drug; and
a color to be applied to the label 12 as required by the medicinal substance labeling standard for the particular drug to be labeled.

The illustrative embodiment of the label 12 in FIG. 4 is compliant with a medicinal substance labeling standard requiring the name 38 of the drug, which is Propofol in the present embodiment, along with a concentration 40 of the drug, which is 10 mg/mL. The name of the drug can be printed using so-called "tall man lettering" to help emphasize the difference between different medicinal substances with similar spellings. Tall man lettering requires printing a distinguishing portion of the name in all caps, and the remainder of the name in common with the distinguished medicinal substance in lower case letters. The label content 36 on the label 12 also includes the identity 42 of the person who prepared the label 12 and/or the syringe of the medicinal substance, along with the date and time 44 the syringe of the medicinal substance was prepared, and the expiration date and time 46 of that syringe of the medicinal substance.

The label 12 also includes a color code that is visible when viewing the content surface 34 of the label 12. For the illustrative embodiment in FIG. 4, the color code appears as a solid colored background 48 to printed text such as the name 38, concentration 40, identity 42 of the preparer, and preparation and expiration dates and times 44, 46. The color code is specified in this example by the medicinal substance labeling standard. For example, induction agents such as thiopental and ketamine are identified by a solid yellow color code. Tranquilizers such as diazepam and midazolam are identified by a solid orange color background. Narcotics such as morphine and fentanyl are identified by a solid blue color background. Antagonist medicinal substances are denoted by diagonal stripes of the agonist color alternating with white stripes.

The color code can optionally be printed onto the content surface 34 as label content 36 by the printer 26. According to alternate embodiments, the color code is pre-applied to the label 12 to be visible when viewing the content surface 34 by a manufacturer of the label stock before the label 12 is introduced to the printer 26. For such alternate embodiments, the appropriate pre-color-coded label stock is selected from among available label stock that is pre-color coded with a plurality of different colors. Each of the different colors corresponds to a different medicinal substance in accordance with the medicinal substance labeling standard. Thus, several rolls of different colored label stock may be available, and the appropriate roll having the color code corresponding to the medicinal substance to be labeled can be selected.

A computer-readable code 50 can also be printed by the printer 26 as label content 36 on the label 12. The computer-readable code can be a barcode, RFID code, or other suitable code that is indicative of the medicinal substance being labeled. For instance, the computer-readable code 50 can represent the other label content 36, and optionally the color code, for integrating the labeling of the syringe or other container with an Anesthesiology Information Management System ("AIMS") or other hospital information system.

Figure 5:
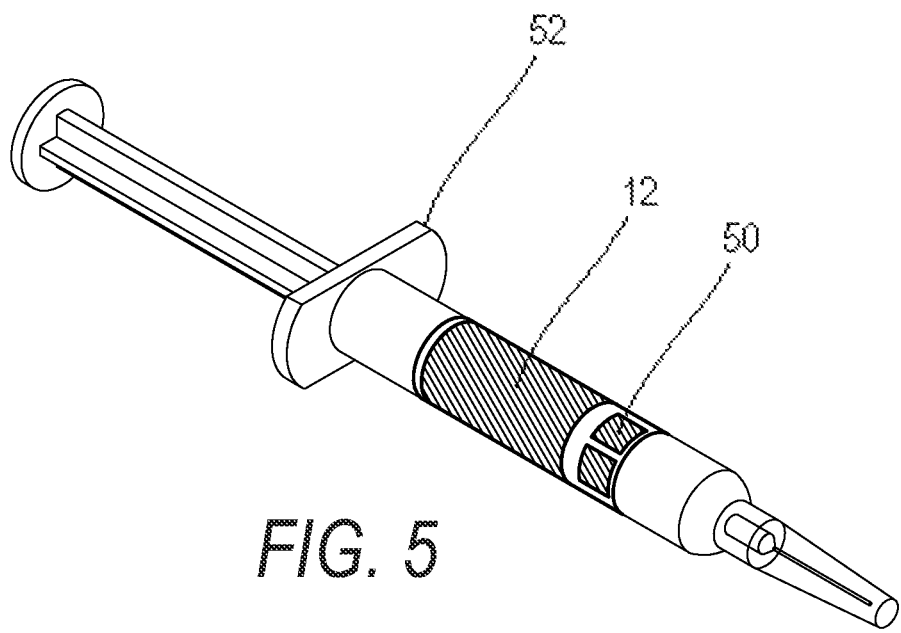
FIG. 5 is a perspective view of a syringe provided with a medical label.

FIG. 5 shows an illustrative embodiment of a syringe 52 storing a drug that is labeled with a label 12 as printed by the OR computer terminal 10. As shown, the label 12 bearing the computer-readable code 50 can be applied to the syringe 52 and, before administration of the drug, the computer-readable code 50 can be scanned by code reader 18 (FIG. 2) provided to the OR computer terminal 10. The OR computer terminal 10 can optionally display the virtual label 16, and optionally audibly announce the drug identified by the label 12 for confirmation purposes. The user can verify the accuracy of the virtual label 16 by pressing a soft key on the display 14 before the label is printed by the printer 26.

Figure 6:
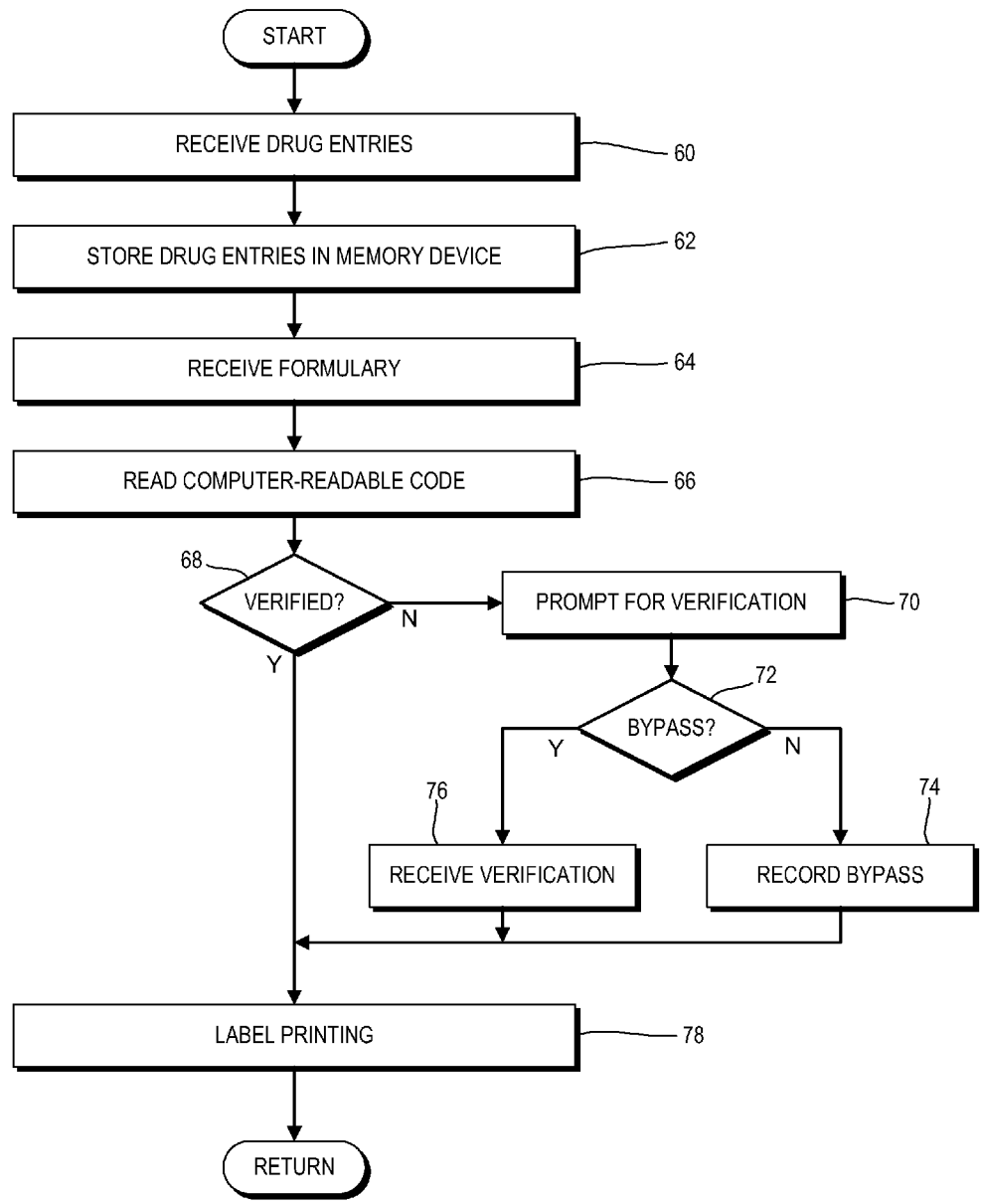
FIG. 6 is a flow diagram.

An example method of confirming drug information is shown in flow diagram form in FIG. 6. In step 60, a plurality of drug entries associated computer-readable codes are received (e.g., received by the OR computer terminal, database server, and/or the pharmacy computer terminal). The plurality of drug entries are stored on a memory device (step 62), such as memory device 24 in the OR computer terminal (FIG. 3), a memory device of the database server, and/or a memory device of the pharmacy computer terminal. A formulary including the plurality of drug entries is created from the MDD and received by the OR computer terminal (step 64). A code reader reads a computer-readable code associated with a drug included among the plurality of drug entries (step 66). In response to reading the computer-readable code, the OR computer terminal determines (step 68) whether the drug associated with the computer-readable code has been verified (before the formulary was received, by manual verification transmitted from another OR computer terminal 10, at the OR computer terminal itself, etc. . . . ). If not, the OR computer terminal 10 automatically prompts the user to verify the drug after the computer-readable code is read by the code reader (step 70). It is then determined (step 72) by the OR computer terminal 10 whether the user has elected to bypass entering manual verification of the unverified drug information. If so, a record is established (step 74) indicating that verification has been bypassed, and any other pertinent information such as the identification of the user who bypassed verification. Input from a user is received, verifying the drug (step 70). If not, manual verification is received (step 76) and the process of printing a label proceeds (step 78). A notification that the drug has been verified can also optionally be transmitted in response to receiving verification at step 76 to a remote, network-connected resource.

If, at step 68, it is determined that the retrieved drug information has been verified, then label printing (step 78) proceeds without prompting the user for verification.

Illustrative embodiments have been described, hereinabove. It will be apparent to those skilled in the art that the above devices and methods may incorporate changes and modifications without departing from the general scope of this invention. It is intended to include all such modifications and alterations within the scope of the present invention. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. An apparatus that stores a formulary, the apparatus comprising:
   a memory device that stores the formulary, the formulary comprising a plurality of drug entries;
   a code reader that reads a computer-readable code associated with a drug container and transmits a signal indicative of data encoded by the computer-readable code;
   a processor adapted to identify, based on the data encoded by the computer-readable code, a first drug entry included in the formulary corresponding to the data encoded by the computer-readable code;
   a presentation device that presents a user with an identity of a drug associated with the first drug entry; and
   a user input device that receives input from the user indicating that the identity of the drug associated with the first drug entry identified from among the plurality of drug entries of the formulary based on the data encoded by the computer-readable code is consistent with information included on a label associated with the drug container;
   wherein, after receiving the input from the user, the processor stores an indication that the identity of the drug has been verified in the formulary.

2. The apparatus of claim 1, wherein the identity of the drug is verified before being entered into the formulary.

3. The apparatus of claim 1, wherein the identity of the drug is verified subsequent to the drug being entered into the formulary.

4. The apparatus of claim 3, wherein after verification of the drug entry in the formulary by the user, the interface device omits further prompting of the user to verify the drug entry in the formulary.

5. The apparatus of claim 1, further comprising an interface device that prompts the user to verify the drug after the computer-readable code that is associated with the drug is read by the code reader.

6. The apparatus of claim 5, wherein the interface device automatically prompts the user to verify a drug entry in the formulary based on a first read of the computer-readable code by the code reader subsequent to the drug entry being entered into the formulary.

7. The apparatus of claim 6, wherein after verification of the drug entry in the formulary by the user, the interface device omits further prompting of the user to verify the drug entry in the formulary upon further reads of the computer-readable code by the code reader.

8. The apparatus of claim 6, wherein after verification of the drug entry in the formulary by the user, the apparatus transmits a notification of the verification to a remote apparatus over a communication network.

9. The apparatus of claim 1, wherein the code reader comprises a barcode scanner, and the computer-readable code comprises a barcode, the apparatus further comprising a printer for printing a label, wherein the label is compliant with a medical labeling standard.

10. The apparatus of claim 1 further comprising a network adaptor that transmits a notification indicating that verification of the drug has occurred using the user input device provided to the apparatus storing the formulary over a communication network addressed to a recipient with authorization to access and edit the formulary.

11. A method of confirming drug information, comprising the steps of:
   receiving a plurality of drug entries that collectively form a formulary, each of said drug entries being associated with a different computer-readable code;
   storing the plurality of drug entries on a non-transitory computer memory device;
   reading, with a code reader, a first computer-readable code associated with a drug container storing a drug included in a first drug entry in the formulary;
   automatically prompting a user to verify that an identity of the drug returned as a result of said reading the computer-readable code with the code reader is consistent with information included on a label associated with the drug container;
   receiving an input from the user verifying the identity of the drug returned based on the computer-readable code is consistent with the information included on the label; and
   after receiving the input from the user, storing an indication that the identity of the drug has been verified in the first drug entry associated with the drug in the formulary.

12. The method of claim 11, wherein said receiving the plurality of drug entries comprises receiving, over a communication network, a formulary including the plurality of drug entries selected from a master drug database at a remotely-located computer terminal.

13. The method of claim 12, wherein said reading, said automatically prompting, and said receiving the input are performed after the formulary is created.

14. The method of claim 11, wherein said automatically prompting is performed only in response to a first reading of the computer-readable code associated with the drug with the code reader, and is not performed in response to a subsequent reading of the computer-readable code.

15. The method of claim 11, further comprising transmitting a notification that the drug has been verified to a remote apparatus over a communication network to notify an administrator authorized to access and edit a formulary comprising the plurality of drug entries that verification of the drug has been received.

16. The method of claim 11, wherein the code reader comprises a barcode scanner, and the computer-readable code comprises a barcode, the method further comprising printing a label that is compliant with a medical labeling standard.

17. The method of claim 16, wherein said receiving the plurality of drug entries comprises receiving a formulary including the plurality of drug entries over a communication network, and replacing an existing formulary, in its entirety, with the formulary received over the communication network.

* * * * *